United States Patent
Cox et al.

(10) Patent No.: US 7,323,343 B2
(45) Date of Patent: Jan. 29, 2008

(54) NITROGEN MONOXIDE, NITROGEN DIOXIDE AND OZONE DETERMINATION IN AIR

(75) Inventors: Richard Anthony Cox, Barton (GB); Roderic Lewis Jones, Cambridge (GB)

(73) Assignee: Cambridge University Technical Services Limited, Cambridge (GB)

(*) Notice: Subject to any disclaimer, the term of this patent is extended or adjusted under 35 U.S.C. 154(b) by 0 days.

(21) Appl. No.: 10/889,824

(22) Filed: Jul. 13, 2004

(65) Prior Publication Data

US 2004/0241868 A1    Dec. 2, 2004

Related U.S. Application Data

(63) Continuation of application No. 09/774,157, filed on Jan. 29, 2001, now abandoned.

(30) Foreign Application Priority Data

Jan. 28, 2000 (GB) .................. 0002081.8

(51) Int. Cl.
*G01N 33/00* (2006.01)
*G01N 27/407* (2006.01)
*G01N 21/76* (2006.01)
*G01N 1/22* (2006.01)
*G01N 27/04* (2006.01)

(52) U.S. Cl. .......... 436/116; 422/52; 422/83; 422/90; 422/93; 422/98; 436/43; 436/52; 436/117; 436/118; 436/135; 436/149; 436/172; 436/181

(58) Field of Classification Search ........ 436/116–118, 436/43, 52, 135, 172, 181, 149; 422/52, 422/83, 98, 93, 90

See application file for complete search history.

(56) References Cited

U.S. PATENT DOCUMENTS 3,840,342 A    10/1974 Neti et al. ............... 436/117

(Continued)

FOREIGN PATENT DOCUMENTS

JP    5-312716    * 11/1993

(Continued)

OTHER PUBLICATIONS

Cox, R. A. et al, International Journal for Chemical Kinetics 1979, 11, 635-648.*

(Continued)

*Primary Examiner*—Arlen Soderquist
(74) *Attorney, Agent, or Firm*—Michael P. Fortkort; Fortkort & Houston P.C.

(57) ABSTRACT

An analytical system is provided for determining nitrogen monoxide, nitrogen dioxide and ozone concentrations in air samples. An ultraviolet light source 4 is used to alter the equilibrium between nitrogen dioxide and oxygen on the one hand and nitrogen monoxide and ozone on the other. Dynamic measurement of ozone concentration with time while ultraviolet irradiation is pulsed enables each gas concentration to be calculated without requiring input gases to be scrubbed. An aApparatus 101 is further provided to provide a controlled flow of gas to a sensor 103 attached to a high altitude balloon while sheltering it from the elements and allowing for affects of temperature, said apparatus comprising a shield 104 and a gas conducting means which uses the venturi effect to control air flow or has a hole to allow water to drain without affecting air flow past the sensor.

34 Claims, 6 Drawing Sheets

U.S. PATENT DOCUMENTS

| | | | | |
|---|---|---|---|---|
| 3,870,468 | A | 3/1975 | Neti | 423/402 |
| 3,977,831 | A | 8/1976 | Fletcher et al. | 436/117 |
| 4,240,798 | A | 12/1980 | Wendelin et al. | 423/219 |
| 4,240,799 | A | 12/1980 | Ryerson | 436/135 |
| 4,335,073 | A | 6/1982 | Sherwood et al. | |
| 5,356,818 | A | 10/1994 | Johnson et al. | |
| 5,540,898 | A | 7/1996 | Davidson et al. | |
| 6,051,436 | A * | 4/2000 | Reagen et al. | 436/106 |
| 6,346,419 | B1 * | 2/2002 | Ryerson et al. | 436/117 |

OTHER PUBLICATIONS

Moortgat, G. K. et al, Journal of the CHemical Society, Faraday Transactions 2 1989, 85, 809-829.*

Nelson, D. D. et al, SPIE 1996, 2834, 148-159.*

Wayne, R. P. et al, Berichte der Bunsen-Gesellschaft 1968, 72, 131-134.□□.*

Butcher, S. S. et al, Analytical Chemistry 1971, 43, 1890-1892.*

McClenny, W. A. et al, Analytical Chemistry 1973, 45, 1514-1518. □□.*

McFarland, M. et al, Chemical Abstracts, 1986, 104, abstract 228027.*

Walega, J. G. et al, SPIE 1991, 1433, 232-241.*

Gao, R. S. et al, Chemical Abstracts 1994, 122, abstract 62719.*

Nelson, D. D. et al, SPIE, 1996, 2834, 148-159.*

Atkins, D. H. F. et al, U. K. At. Energy Res. Estab., Rep. (1973), AERE-R 7615, 22 pages.*

Jenkin, M. E. et al. Journal of Physical Chemistry 1985, 89, 192-199.*

McFarland, M. et al, Journal of Geophysical Research 1986, 91, 5421-5437.*

Gao, R. S. et al, Journal of Geophysical Research 1994, 99, 20,673-20,681.*

Wang, T. et al, Journal of Geophysical Research 1996, 101, 28,991-29,004.*

Jenkins, M. E. et al. Transport and Chemical Transformation of Pollutants in the Troposphere 1997, vol. 3, 120-127, Editor: Le Bras, Georges; Publisher: Springer, Berlin, Germany.*

Hinsch, H. et al, Applied Optics 1971, 10, 1406-1411.*

Kley, D. et al, Atmospheric Technology 1980, 12, 63-69.*

Guicherit, R., "Ozone Analysis by Chemiluminescence Measurement," Z. Anal. Chem., vol. 256, 1971, pp. 177-182.

Stuhl, F. et al., "Measurements of Rate Constants for Termolecular Reactions of O($^3$P) with NO, O$_2$, CO, N$_2$, and CO$_2$ Using a Pulsed Vacuum-uv Photolysis-Chemiluminescent Method," *The Journal of Chemical Physics*, vol. 55, No. 8, 1971, pp. 3943-3953.

Guicherit, R., *Chemcial Abstracts*, vol. 78, 1973, abstract 7421g.

Burrows, J.P. et al., "Modulated Photolysis of the Ozone-Water Vapour System: Kinetics of the Reaction of OH with H$_2$O," *Journal of Photochemistry*, vol. 16, 1981, pp. 147-168.

Dickerson, Russell R. et al., *Chemical Abstracts*, vol. 96, 1982, abstract 1285In.

Ortman, Gordon C., *Chemical Abstracts*, vol. 97, 1982, abstract 27858a.

Johnston, H.S. et al., *Proceedings of the National Academy of Sciences of the United States of America*, vol. 57, 1967, pp. 1146-1153.

Stephens, Edgar R. et al., "Atmospheric Photochemical Reactions in a Tube Flow Reactor," *Atmospheric Environment*, vol. 3, 1969, pp. 573-582.

Guicherit, R., "Indirect Determination of Nitrogen Oxides by a Chemiluminescence Technique," *Atmospheric Environment*, vol. 6, 1972, pp. 807-814.

Cox, R. Anthony et al., "Kinetics of Chlorine Oxide Radical Reactions Using Modulated Photolysis," *Journal of the Chemical Society, Faraday Transactions 1*, vol. 75, 1979, pp. 1635-1647.

Ortman, Gordon C., "Ozone Precursor Monitor (OPM) for Investigating Air Pollution," *Analysis Instrumentation*, vol. 20, 1982, pp. 65-84.

Dickerson, Russell R., "Direct Measurement of Ozone and Nitrogen Dioxide Photolysis Rates in the Troposphere," *Journal of Geophysical Research*, vol. 87, No. C7, 1982, pp. 4933-4946.

Rowley, David M., et al., "The UV-Visible Absorption Cross-Sections and Atmospheric Photolysis Rate of HOI," *Journal of Atmospheric Chemistry*, vol. 34, 1999, pp. 137-151.

Hall, Ian W., "Kinetics of the Reaction of NO$_3$ with HO$_2$," *Journal of Physical Chemistry*, vol. 92, 1988, pp. 5049-5054.

* cited by examiner

NITROGEN MONOXIDE, NITROGEN DIOXIDE AND OZONE DETERMINATION IN AIR

STATEMENT OF RELATED APPLICATION

This application is a continuation and claims the benefit of priority from U.S. patent application Ser. No. 09/774,157, filed Jan. 29, 2001, now abandoned, entitled "Air Content Determination", which is incorporated herein by reference in its entirety.

FIELD OF THE INVENTION

This invention relates generally to devices and methods for the detection of atmospheric components and, in particular, to devices and methods for the detection of. Atmospheric components of particular interest are nitrogen dioxide, nitrogen monoxide and ozone.

BACKGROUND

In recent years, with increased concern over environmental issues, there is more and more need for accurate and cost effective measurement devices and methods for the detection of gases in the atmosphere. There is a demand both for measurements of pollutant gases at ground level, due to their direct effect on human health, and also within the atmosphere for atmospheric analysis and research.

Ozone, nitrogen dioxide and nitrogen monoxide are gases of particular relevance and it is desirable to monitor concentrations of these gases in air. Particular applications include roadside monitoring and atmosphere content monitoring.

The paper "Indirect Determination of Nitrogen Oxides by Chemiluminescence Techniques" (R. Guicherit, Atmos Environ. 1972 November; 6(11) p. 807-14)REFERENCE, 1972) shows a method and apparatus for determining nitrogen dioxide in air samples. This process involves use of a chemiluminescent detection system for ozone, which is produced by means of the effect of ultraviolet light on the equilibrium reaction:

$$NO_2 + O_2 \leftrightarrows NO + O_3$$

Ultraviolet light pushes the equilibrium to the right, forming nitrogen monoxide and ozone. This process involves irradiating a gas sample with ultraviolet light and then determining the final ozone concentration.

The resulting system is complex and the authors found it essential to pass incoming gas through scrubbers to remove ozone and to oxidise nitrogen monoxide to nitrogen dioxide before beginning irradiation.

This system further proposed that, once nitrogen dioxide had been determined, the concentration of nitrogen monoxide could subsequently be calculated after a separate reading of ozone produced by ultraviolet irradiation of a separate gas sample, scrubbed as before, with the addition of a further scrubber to remove ozone.

This process is the basis of a number of gas monitoring devices on sale at the present time. However, these devices are expensive (in the order of £10,000), complex and suffer from limitation in stability with time and in response to temperature changes.

Another known technique for determining total nitrogen oxide content in air is described in U.S. Pat. No. 3,973,914 to van Heusden. This functions by converting nitrogen dioxide to nitrogen monoxide which is then determined by monitoring chemiluminescence of the reaction between nitrogen monoxide and excess ozone. This functions by converting nitrogen dioxide to nitrogen monoxide which is then determined by monitoring chemiluminescence of the reaction between nitrogen monoxide and excess ozone.

This process is the basis of a number of gas monitoring devices on sale at the present time. However, these devices are expensive (in the order of £10,000), complex and suffer from limitations, particularly relating to the quantitative conversion of nitrogen dioxide to nitrogen monoxide.

A first aim of the present invention is to provide a cheaper, simpler and more reliable gas monitoring device, capable of accurate determination of nitrogen dioxide, nitrogen monoxide and/or ozone in air.

One use for a cheaper, simple and more reliable gas monitoring device would be for measuring atmospheric composition at high altitudes. Typically, this is carried out by attaching sensors to a helium filled weather balloon and to launch the balloon into the atmosphere. The sensor then transmits data, usually via a radio link, as the balloon passes up through the atmosphere. The fact that the sensor is attached to a balloon places severe restrictions in terms of weight and cost on the sensor design. The cost aspect can be particularly critical, because generally such sensors have to be treated as disposable, given that they may be difficult to locate once they fall back to the ground. All of this can make it extremely difficult to produce a sensor which provides appropriately accurate readings that are continuous throughout the ascent of the balloon and which is capable of resisting the effects of high altitude and low temperature, where contaminants such as rain ice can affect sensor output.

Therefore, a second aim of the present invention is to provide a device that is suitably reliable, cheap and light to benefit high altitude gas monitoring.

Furthermore, high altitude gas measurement systems usually use a pump to draw air into a sensing arrangement. The pumps are expensive, relatively heavy and require considerable power to operate, increasing overall device weight.

Furthermore, with such sensors it can often be difficult to provide accurate readings because it is difficult to determine exactly the rate at which atmospheric air is flowing over the sensor and a further aim of the present invention is to provide sensing apparatus which mitigates this problem.

SUMMARY OF THE INVENTION

According to a first aspect of the present invention, there is provided an instrument for assaying the concentration of one or more of nitrogen dioxide, nitrogen monoxide and/or ozone in an air sample; t; the instrument comprising an equilibrium altering means for changing, or an element adapted to change, the equilibrium between nitrogen monoxide and nitrogen dioxide in the presence of ozone and oxygen, and a first gas sensor for quantifying the concentration of a first gas, being one of nitrogen dioxide, nitrogen monoxide or ozone; the instrument being adapted to measure the concentration of the first gas whilst the equilibrium between nitrogen monoxide and nitrogen dioxide in the presence of ozone and oxygen is altered and thereby to calculate the concentration of nitrogen dioxide, nitrogen monoxide and/or ozone in the air sample.

Preferably, the equilibrium altering means comprises an ultraviolet light source. More preferably, the ultraviolet light source is switched on and off periodically.

The equilibrium altering means may comprise a means for adding, or an element adapted to add, one or more of nitrogen monoxide, nitrogen dioxide or ozone, and/or.

The equilibrium altering means may comprises a means for removing, or an element adapted to remove, one or more of nitrogen monoxide, nitrogen dioxide, ozone or oxygen.

Preferably, the instrument is adapted to measure the concentration of the first gas at a plurality of time points and thereby monitor the rate at which the balance between nitrogen dioxide and nitrogen monoxide changes in response to the effects of the equilibrium altering means.

Typically, the first gas sensor is an ozone sensor.

The instrument may be adapted to allow for the effects of temperature and/or pressure on the equilibrium between nitrogen dioxide and nitrogen monoxide.

According to a second aspect of the present invention there is provided a method of calculating the concentration of nitrogen dioxide, nitrogen monoxide and/or ozone in air, the method comprising the steps of:

activating an equilibrium altering means for changing, or an element adapted to change, the equilibrium between nitrogen monoxide and nitrogen dioxide in the presence of ozone and oxygen in an air sample;

taking three or more readings of the concentration of a first gas, being one of nitrogen dioxide, nitrogen monoxide or ozone including at least one reading taken before the changes caused by the equilibrium altering means reach a steady state; and thereby calculating the concentration of nitrogen dioxide, nitrogen monoxide and/or ozone in the air sample.

Preferably, the equilibrium altering means is an ultraviolet light source.

Preferably, the method includes the step of switching the ultraviolet source on and off periodically.

The equilibrium altering means may comprise a means for adding, or an element adapted to add, one or more of nitrogen monoxide, nitrogen dioxide or ozone.

The equilibrium altering means may comprise a means for removing, or an element adapted to remove, one or more of nitrogen monoxide, nitrogen dioxide, ozone or oxygen.

The concentration of the first gas at a plurality of time points may be used to calculate the rate at which the balance between nitrogen dioxide and nitrogen monoxide changes in response to the effects of the equilibrium altering means.

The readings may be of ozone concentration.

The method may further include the step of allowing for the effects of temperature and/or pressure on the equilibrium between nitrogen dioxide and nitrogen monoxide.

According to a third aspect of the present invention there is provided a computer program comprising program instructions which, when loaded onto a computer, are adapted to calculate, or constitute a processing means for calculating, the concentration of nitrogen monoxide, nitrogen dioxide and/or ozone in an air sample by the method of the second embodiment.

According to a fourth aspect of the present invention there is provided a computer program according to the third aspect embodied on a record medium.

According to a fifth aspect of the present invention there is provided sensing apparatus for detecting components in atmospheric air as the sensor is drawn up through the atmosphere, the sensor comprising:

a sensor element;

shielding means for shielding, or an element adapted to shield, the sensor element from direct contact with air flow as the sensor is drawn through the atmosphere; and means for diverting, or an element adapted to divert, air through the shielding means and over the sensor element as the sensor passes through the atmosphere.

Preferably, the means for diverting air comprises a gas conducting member shaped to provide a pressure differential across the shielding means and cause air to move through the shielding means.

The gas conducting member may be shaped to provide a low pressure region at an entry to the shielding means and thereby draw air through the shielding means into the gas conducting member.

The gas conducting member may comprise a flow restricting member for diverting air that flows through the gas conducting member in use into the shielding means.

The sensing apparatus may have an aperture to allow water or ice to flow out of the gas conducting member.

According to a sixth aspect of the present invention there is provided sensing apparatus comprising:

a sensor element;

means for regulating, or an element adapted to regulate, the temperature of the sensor element by providing heat energy to the sensor element; and means for calculating the air flow across the sensor element from the amount of heat energy supplied to the sensor element.

The sensor apparatus may further comprise a means for measuring, or an element adapted to measure, the temperature of the sensor.

DESCRIPTION OF THE FIGURES

Examples of the present invention will now be described with reference to the accompanying drawings, in which.

DETAILED DESCRIPTION OF THE INVENTION

Figure 1:
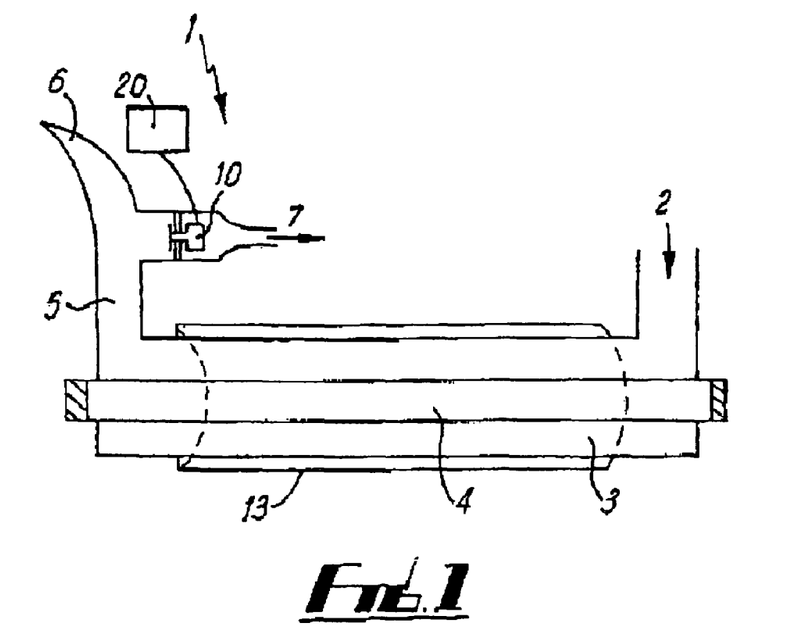
FIG. 1 is a schematic diagram of an analytical system according to the present invention.

FIG. 1 shows an example analytical system according to the present invention.

The analytical system shown generally as 1 comprises an air inlet 2 which allows an air sample to enter irradiation chamber 3. The irradiation chamber 3 comprises an ultraviolet source 4 and may be encased by an ultraviolet reflective surface 13 such as a metal foil. There is a chamber outlet 5 from the irradiation chamber, which incorporates a UV light trap 6. Air passes from the chamber outlet 5 to an external outlet 7 via an ozone sensor 10. A pump (not shown) or airflow control means as discussed below may be provided to draw air through the external outlet 7 and through the sensor as a whole.

Within the irradiation chamber, ultraviolet light from the ultraviolet source 4 irradiates the air sample, driving the below reaction towards the formation of ozone and nitrogen monoxide:

$$NO_2 + O_2 \rightleftharpoons NO + O_3$$

By positioning an ozone sensor 10 downstream from the ultraviolet source 4, readings can be taken of ozone levels after the equilibrium has been affected by irradiation (or other means discussed below).

A processing means 20 such as a computer, microprocessor or other device having storage and processing capacity is provided to analyse the measurements and compute gas concentrations in the input gas sample. The invention further extends to the software used by said processing means 20 to control the switching on and off of the ultraviolet light source, record gas concentration readings from the sensor 10 and carry out gas concentration calculations. Said software may be provided on a digital storage means such as a magnetic or optical disk or solid state storage device such as EEPROMk.

The basis of the present invention is that readings of ozone concentration are taken not simply after the ratio of nitrogen monoxide to nitrogen dioxide has been modified by the influence of ultraviolet light or other factors and a steady state has been reached, but also either (a) during the process of this ratio being altered or (b) after or during the application of two different means for altering the ratio. The resulting readings are then used to calculate the concentrations of nitrogen monoxide, nitrogen dioxide and ozone in the gas sample.

The kinetics of the underlying reaction can be summarised as follows:

$$d[O_3]/dt = J_1[NO_2] - k_2[NO][O_3]$$

where $[O_3]$ is the instantaneous concentration of ozone, $[NO_2]$ is the instantaneous concentration of nitrogen dioxide, and $[NO]$ is the instantaneous concentration of nitrogen monoxide, $J_1$ is rate coefficient for photolysis of $NO_2$, in units of per second, and $k_2$ is the rate constant for the reverse reaction.

At equilibrium steady state:

$$[O_3] = J_1[NO_2]/k_2[NO]$$

Characteristic time, $\tau$, to equilibrium is given by:

$$\tau = (J_1 + k_2[NO])^{-1}$$

Both equilibrium steady state ozone concentration and characteristic time can be readily deduced either from monitoring the ozone concentration curve with time or from several individual ozone readings at different times by well-known mathematical methods.

Case 1: In the Sunlit Atmosphere:
Typically $[O_3] = 50$ ppb—in excess over NO
$J_1 = J_{Sunlight}$ $(= 10^{-2}\ s^{-1})$
$\tau = (10^{-2} + 5 \times 10^{-4}\ [NO]\ (ppb))^{-1}$ s,.
and so $\tau \lessapprox <100$ secs Case 2: In the Instrument Under Photolysis:
$J_1 = J_{NO2}$ $(= 0.1\ s^{-1})$
$\tau = (10^{-1} + 5 \times 10^{-4}\ [NO])^1$
and so $\tau \lessapprox <10$ secs Case 3: In the Dark:
$J_1 = 0$ Therefore, in the dark, the atmospheric steady state relaxes towards a state where [NO] (or $O_3$) tends to zero with $\tau = (5 \times 10^{-4}\ [NO])^{-1}$ or $(5 \times 10^{-4}[O_3])^{-1}$ depending on which gas is present in excess. Therefore, typically $\tau > (2.5 \times 10^{-2})^{-1} > \geqq 40$ secs.

If, however, concentrations of [NO] and $[O_3]$ are similar, it will be clear to one skilled in the art that you instead get a complex but mathematically definable rate of ozone loss.

By monitoring the ozone concentration in response to periodic light and dark and application of standard computing techniques it is therefore possible to get information about all three components $[O_3]$, $[NO_2]$ and $[NO]$.

Figure 2:
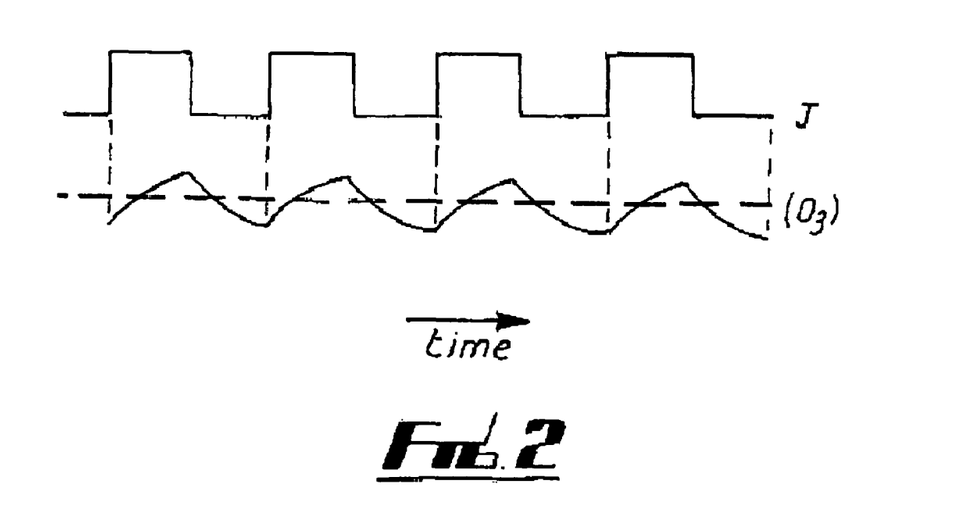
FIG. 2 shows the response with time of ozone concentration in response to periodic ultraviolet irradiation, J.

In a preferred embodiment, light is pulsed as shown in FIG. 2 which illustrates the periodic alteration of J with time and the resulting ozone concentration. Clearly the precise pulse shape of ozone concentration will depend on the gas flow rate, length of the ultraviolet irradiation zone, spectrum and intensity of ultraviolet source, gap between the end of irradiation zone and sensor and other calculable parameters.

Therefore, $d[O_3]/dt$ under instrument irradiation can be used to give the concentration of nitrogen dioxide in the air sample.

Measurement of ozone concentration after short sample time in dark gives the ozone concentration in the air sample.

The concentration of ozone after full relaxation in the dark gives the difference between sample ozone and nitrogen monoxide concentrations.

The characteristic relaxation time in the dark of an unphotolysed air sample gives the nitrogen monoxide concentration.

The characteristic relaxation time of a photolysed air sample gives the sum of the concentrations of nitrogen monoxide and nitrogen dioxide.

The time resolved measurement of ozone therefore allows rates and relaxation time to be determined and so the concentrations of nitrogen monoxide, nitrogen dioxide and ozone can be determined.

Temperature has an effect on the value of $k_1\ J_1$. The corresponding chemical step has a small activation energy thus temperature effects are small. If temperature effects need to be corrected this can be done using a simple measurement of temperature from a temperature measuring means (not shown). Pressure will have a still smaller effect and will preferably not be taken into account; however, it could be readily corrected for if required using readings from a pressure gauge (not shown). Pressure has a linear effect on the measured concentration for some types of ozone sensor as the partial pressure of ozone changes linearly with pressure but the concentration of ozone does not. This can readily be allowed for by well known software methods.

Low frequency phase sensitive detection might be an approach to allow determination of relaxation time and the information can be processed to give improved sensitivity.

FIGS. 3 and 4 show the concentration of nitrogen monoxide, nitrogen dioxide and ozone with time (in seconds) for various simulated experiments at 298 Kelvin, 1 atmosphere pressure, $k = 0.06$ per second.

In these calculations, it is recognised the underlying chemical reactions are:

$k_1$ $NO_2 h\nu \rightarrow NO + O$

Figure 3A:
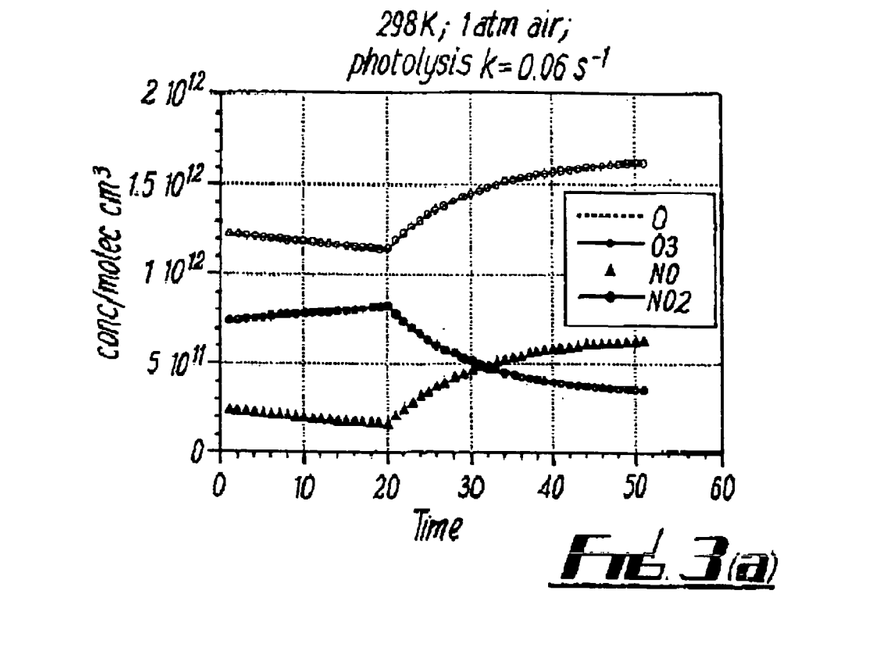
FIG. 3 shows the simulated variation of ozone, nitrogen monoxide and nitrogen dioxide concentrations in response to specific changes to the level of ultraviolet irradiation.

FIG. 3a shows the response to 20 seconds in the dark and 30 seconds of photolysis starting with initial gas concentrations of 30 ppb $NO_2$, 10 ppb NO and 50 ppb $O_3$.

Figure 3B:
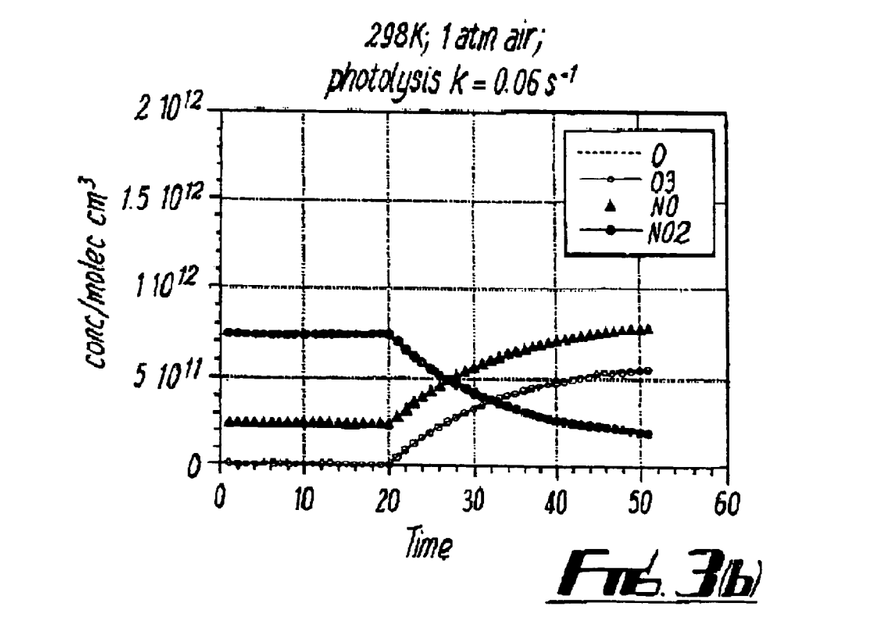

FIG. 3b shows the equivalent situation starting with 30 ppb $NO_2$, 10 ppb NO and 0.5 ppb $O_3$.

Figure 3C:
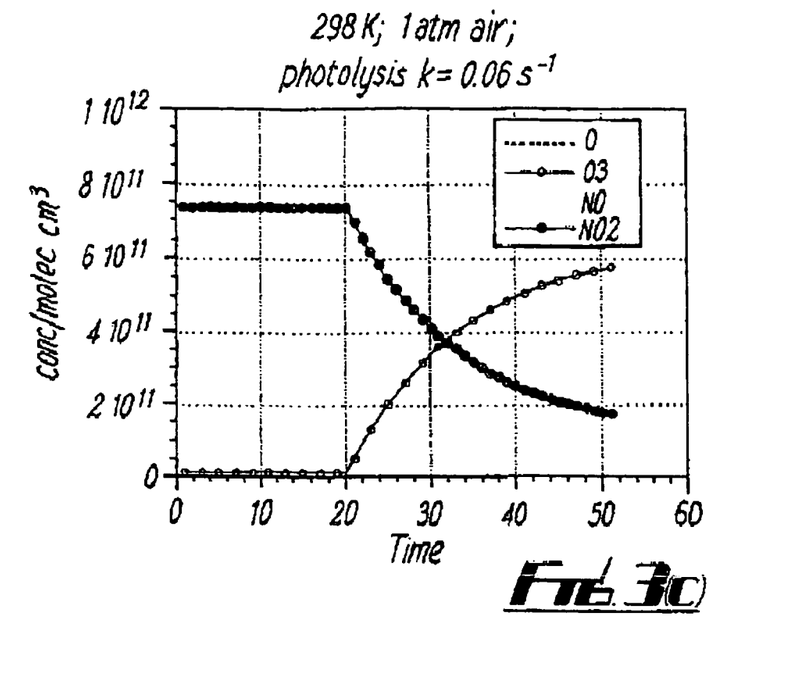
Figure 3D:
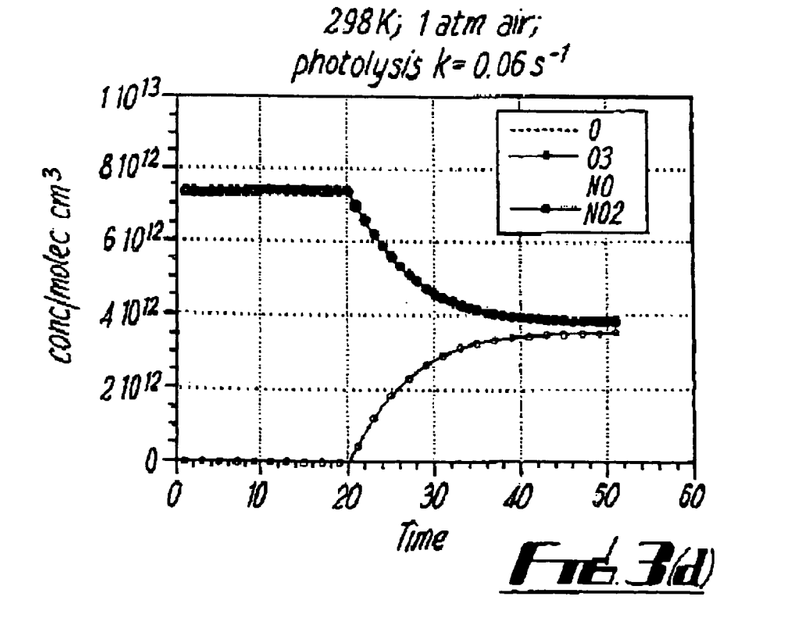
Figure 4A:
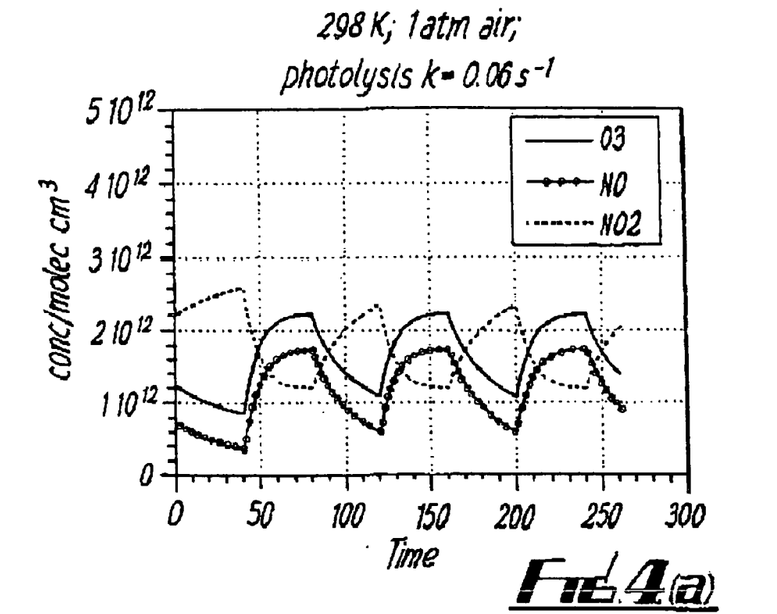
FIG. 4 shows the simulated variation of ozone, nitrogen monoxide and nitrogen dioxide concentrations in response to specific periodic changes to the level of ultraviolet irradiation.
Figure 4B:
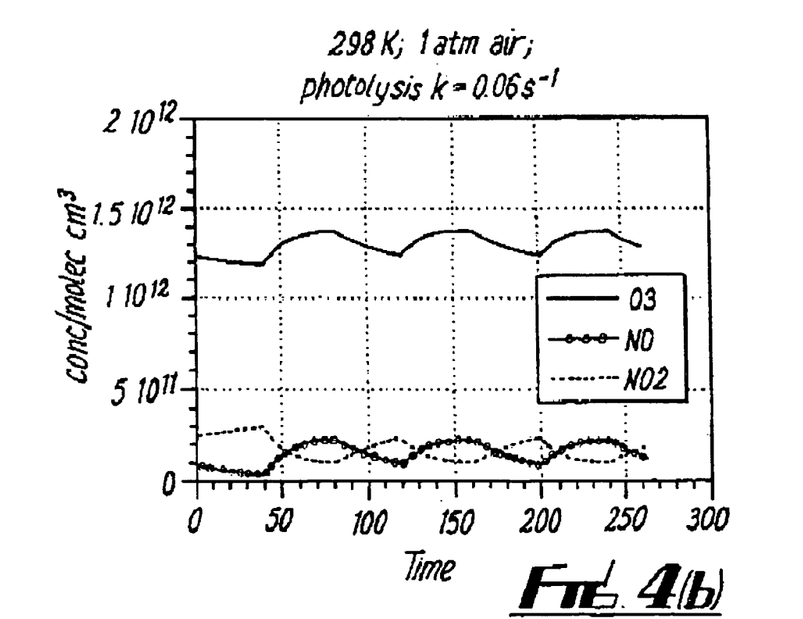

FIGS. 3c and 3d show the equivalent ozone and nitrogen dioxide concentrations with time for s3c starting concentrations 30 ppb $NO_2$, 0.5 ppb NO, 0.5 ppb $O_3$ (a3(c)) and in the case of FIG. 3d 300 ppb $NO_2$, 0.5 ppb NO, 0.5 ppb $O_3$ (3(d)). FIGS. 4(a) and 4(b) shows the ozone, nitrogen monoxide and nitrogen dioxide traces with time in response to repeating patterns of 40 seconds in the dark and 40 seconds of photolysis. In the case of FIG. 4(a), the starting concentrations are 90 ppb $NO_2$, 30 ppb NO and 50 ppb $O_3$. In the case of FIG. 4(b) the starting concentrations are 10 ppb $NO_2$, 30 ppb NO and 50 ppb $O_3$.

Figure 4C:
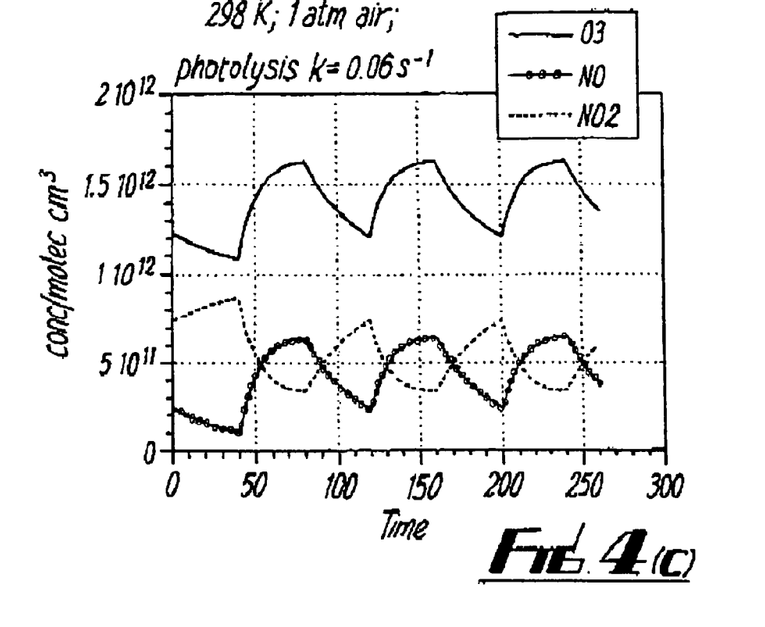
Figure 4D:
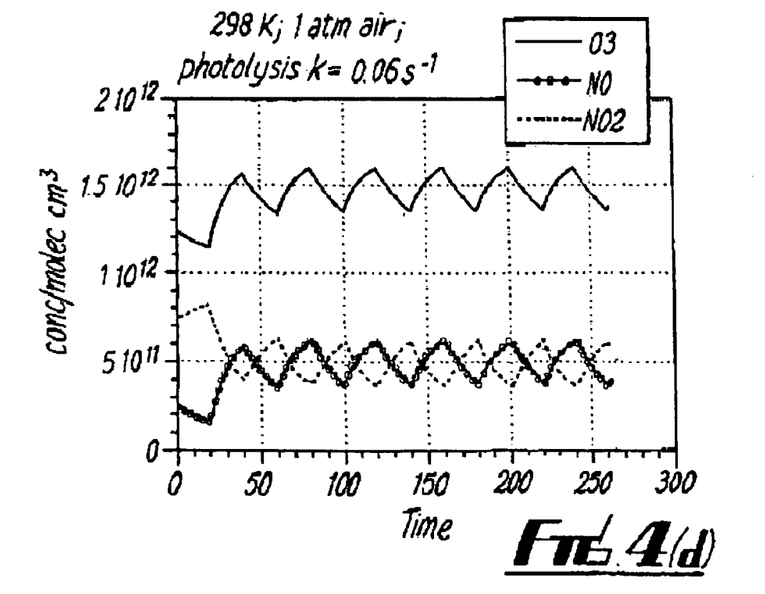

In FIG. 4(c) the starting concentrations are 30 ppb $NO_2$, 10 ppb NO and 50 ppb $O_3$. FIG. 5b 4(d) shows the corresponding situation for a periodicity of 20 seconds in the dark in then 20 seconds photolysis.

Ozone levels can be monitored throughout the reaction to give a time course or, alternatively, the ultraviolet light source can be pulsed for different durations and individual readings taken after each duration pulse then used to form the equivalent time course.

This system can therefore readily establish the concentrations of nitrogen monoxide, nitrogen dioxide and ozone concentrations without needing to pre-treat the sample or wait for a steady state to be reached. (Oxygen is essentially constant and in excess). Prior art methodology measures only a steady state ozone concentration after prolonged irradiation and requires two gases to be scrubbed to make the calculation possible. However, by making three or more independent measurements in different conditions, all three gases can be established without having to scrub the input gas sample.

Examples of suitable ultraviolet sources 4 would be a fluorescent xenon tube, mercury lamp, deuterium lamp, sunlight (perhaps focused through a lens into a reflective cavity), frequency doubled laser or future ultraviolet light source. Indeed, a violet/ultraviolet light emitting diode/ diode laser would be ideal if practical devices of this type become available. An ultraviolet light photosensor may be provided to quantify ultraviolet light produced.

Several different types of ozone sensor would be suitable. For example, the amperometric type using an aqueous electrolyte and operating at room temperature. Such sensors can be obtained from EN-SCI Inc of Boulder, Col., USA and City Technology Ltd of Portsmouth, UK. Solid state semiconductor sensors with a resistance which changes when exposed to ozone could be used. These operate around 500° C. and examples include the LGL52 Ozone sensor from Capteur Ltd of Didcot, UK. Stain tubes which change colour when exposed to ozone may be used. These indicate ozone concentration through the depth to which a colour change occurs but are not particularly accurate. Such devices can be obtained from Drägerwerk GmbH in Lubeck, Germany. Other possible ozone sensors include $In_2O_3$ coated surface acoustic wave devices and phthalocyanines. Non-aqueous electrolyte amperometric ozone sensors are available from Sensoric GmbH in Bonn, Germany.

In an alternative embodiment, nitrogen dioxide or monoxide might be measured instead by means of a suitable sensor. For example, amperometric nitrogen monoxide and nitrogen dioxide sensors which operate at room temperature are sold by City Technology of Portsmouth, UK.

It will be clear to one skilled in the art that an air sample could be trapped in a volume, irradiated and then monitored in situ; however, it is preferred to maintain a flow of air.

In an alternative embodiment, instead of altering the length of time for which a gas sample is irradiated, the equilibrium between nitrogen monoxide and nitrogen dioxide may be altered by other equilibrium altering means. Therefore, instead of or combined with an ultraviolet light source, there may be provided any other means for affecting the equilibrium between nitrogen dioxide and nitrogen monoxide. For example, nitrogen dioxide, nitrogen monoxide, oxygen or ozone could be added by a gas source or removed by a scrubber. Nitrogen dioxide, nitrogen monoxide or ozone could undergo a chemical reaction, including for example conversion of nitrogen dioxide to nitrogen monoxide using a heated coil, e.g. of platinum/rhodium. Temperature and, to a lesser extent,and pressure, can also affect the equilibrium and these can be varied to give different treatments of the gas sample and therefore measurements of equilibrium with different values of J and $k_1$. The different position of the equilibrium and/or different characteristic relaxation time under different conditions provides further independent measurements which can be used to calculate all three gas concentrations.

Although calculations are shown which involve the intermediate step of calculating equilibrium steady state concentration of ozone and characteristic time to equilibrium, it will be immediately clear to one skilled in the art that equivalent mathematical calculations may be used to give the required sample gas concentrations and a particular method of calculation can be selected by one skilled in the art.

It may further be taken into account in the calculations that incoming nitrogen monoxide and nitrogen dioxide will be in equilibrium already, although this depends on the ambient ultraviolet level. Given that air oxygen is present in a constant excess (albeit one which varies with altitude) this further constraint could improve the accuracy of the calculations. In this case an external ultraviolet light photosensor might be used to quantify the level of ultraviolet light experienced externally by the gas sample.

Further sensors, such as an ozone sensor (not shown) besides the inlet 2 may allow further accuracy, although this is not required in the present invention.

It will be clear that a controlled rate of gas flow through the sensor is important. In weather balloons, the weight of a conventional pump is prohibitive.

Figure 5:
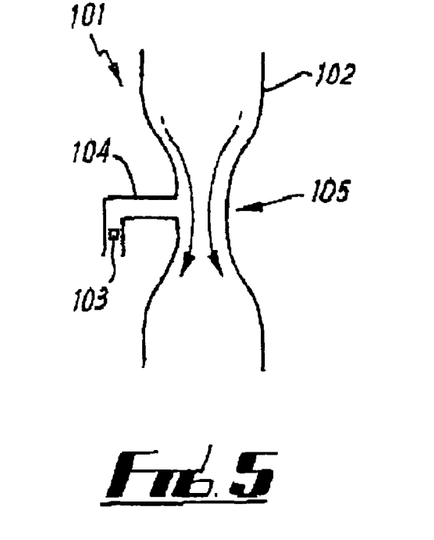
FIG. 5 is a schematic cross-section through an example sensing apparatus.

Referring to FIG. 5, a sensing apparatus 101 according to the invention is configured to be attached to a weather balloon (not shown) so that, in use, it can be drawn up through the atmosphere by the weather balloon. The arrow in the diagram indicates the direction of air flow through the sensing apparatus 101 when in use. The sensing apparatus 101 has a gas conducting member 102 which has a shape such that its diameter in its central portion is less than that at either of its ends. Such a configuration generates, in use, a region of low pressure in the central narrow region of the gas conducting member 102 by the well-known Venturi effect. It will be recognised by one skilled in the art that many configurations of gas conducting member 102 would provide said region of low pressure, although an elongate pipe is preferred, particularly broadly cylindrical hourglass- s shape is preferredhaped pipe.

Figure 6:
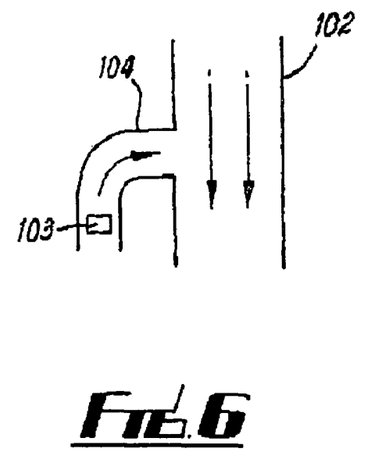
FIG. 6 is an expanded view of a section of FIG. 5.

In the central region there is positioned a sensor element 103 and a shield member 104 which protects the sensor element 103 from damage due to hailstones, heavy rain, etc during use. The shield 104 is arranged such that it connects to the central region of the gas conducting member 102. Referring to FIG. 6, in use, the low pressure region generated in the gas conducting member 102 draws air into the shield 104 and over the sensor element 103 using, for example, King's Law. In this example the sensor element 103 is configured to detect ozonean ozone detector but it is also possible to detect other atmospheric matter.

The shield member 104 maybe connected directly to the external outlet 7 of the sensor shown in FIG. 1 but this sensing apparatus 100 may be used with any type of sensor element 103 for detection of different gases.

Figure 7:
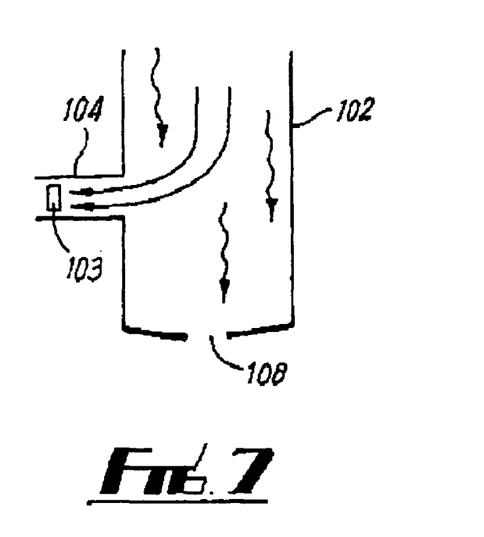
FIG. 7 is a schematic cross-section through an alternative sensing apparatus.

Instead of using a low pressure region to draw air through the shield 104, the invention also encompasses the use of a high pressure region to drive air through the shield 104 and past the sensor element 103. FIG. 7 shows a second examplean example of a gas conducting member which provides such a high pressure region., Cin which components corresponding to those in FIG. 5 are numbered identically. In this example a constricting member is provided at what is, in use, the lower end of gas conducting member 102. The constriction has a narrow opening 108 and tapered base to allow particles such as rain and ice to fall out of the cylindrical member 102, but is narrow enough to direct air through the shield 104 and over sensor 103. Other configurations of gas conducting member to provide low or high pressure regions will now be apparent to one skilled in the art.

Figure 8:
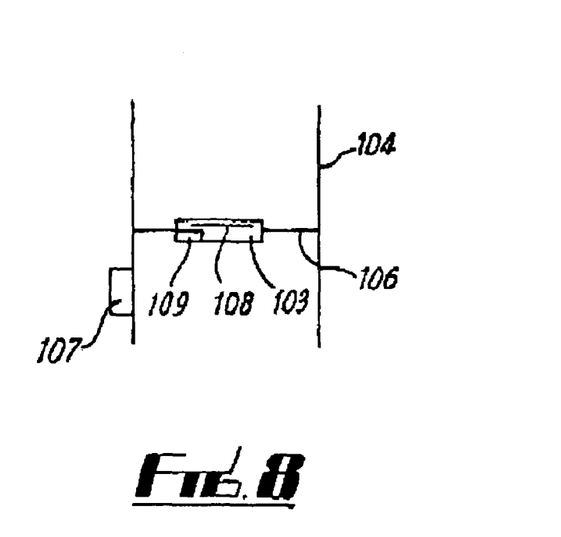
FIG. 8 is a schematic cross-section through a further sensing apparatus.

FIG. 8 shows a detail of a sensor element 103 in a shield 104. In this example the air flow over the sensor element 103 may be generated by a device shown in FIGS. 5 or to 7 or by more conventional positioning of the sensor element within a known sensor devicemanifold. It does, however, have particular benefits in the configuration shown in FIGS. 5 to 7.

Many sensors elements are sensitive to air flow and it is important to know to be able to either fix or measure the air flow past such sensors. It is desirable to do this in such a fashion as to minimise the number, cost and weight of instruments and apparatus.

Some sensor elements, particularly tungsten oxide detectors for ozone have to be maintained at a high temperature relative to the surrounding air. For example, a tungsten oxide sensor will typically be maintained between 500-600° C. in air which is between 200 and 300° K. These sensors are mounted on hot wires and the power supplied to the sensors is altered using standard feedback techniques to maintain sensor element temperature.

In this example, the sensor element 103 is supported by electrical connecting wire 106 which connects to a sensor driving and monitoring device 107. The wires provide electrical energy to a heating element (not shown)108 on the sensor 103 or adjacent to the sensor element 103 itself, causing the sensor element 103 to be heated as is standard. Airflow over the sensor element 103 when the sensor 101 is in use cools the sensor element 103 and the actual temperature of the sensor element 103 can be determined by a temperature sensor (not shown).109.

However, as the primary source of cooling of the sensor element 103 is the passing air and as this depends in a calculable relationship on the speed of the passing air, this invention recognises that the amount of power required to maintain the temperature of the sensor can be used to calculate the rate of cooling of the sensor due to passing air and therefore the speed of said passing air.

The output of the temperature sensor, together with the electrical energy input to heat the sensor element 103 is determined by the sensor element driving means 107 and used to calculate the air flow over the sensor element 103. This air flow data is useful not just to improve the accuracy of readings from the sensor element 103 but also in for determining other operating parameters and to increase the accuracy of readings. parameters.

Further alterations and modifications may be made within the scope of the invention herein disclosed. Accordingly, the scope of the present invention should be construed solely by reference to the appended claims.

The invention claimed is:

1. An instrument for quantifying the concentration of nitrogen dioxide, nitrogen monoxide and ozone in an air sample, the instrument comprising:
    a conduit equipped with an inlet and an outlet and adapted to permit a flow of gas from said inlet to said outlet;
    an equilibrium altering means for changing the kinetic equilibrium within the conduit between nitrogen monoxide and nitrogen dioxide in the presence of ozone and oxygen;
    a control means for modulating the equilibrium altering means; and
    a first gas sensor for quantifying the concentration of a first gas selected from the group consisting of nitrogen dioxide, nitrogen monoxide and ozone;
wherein the first gas sensor is positioned within the conduit and downstream from the equilibrium altering means, wherein the instrument is adapted to take readings of the concentration of the first gas with the first gas sensor and at a plurality of time points and to use those readings to calculate the concentration of nitrogen dioxide, nitrogen monoxide and ozone in the air sample, and wherein some of said plurality of time points occur during the alteration of the kinetics between nitrogen monoxide and nitrogen dioxide in the presence of ozone and oxygen.

2. The instrument of claim 1, wherein the equilibrium altering means comprises an ultraviolet light source.

3. The instrument of claim 2, wherein the ultraviolet light source is switched on and off periodically by the control means.

4. The instrument of claim 2, wherein the control means is further adapted to allow for the effects of at least one factor, which factor is selected from the group consisting of temperature and pressure, on the kinetics between nitrogen dioxide and nitrogen monoxide.

5. The instrument of claim 1, wherein the equilibrium altering means comprises a means for removing one or more of nitrogen monoxide, nitrogen dioxide, ozone or oxygen.

6. The instrument of claim 1, wherein the first gas sensor is an ozone sensor.

7. The instrument of claim 1, wherein some of said plurality of time points occur after the kinetics between nitrogen monoxide and nitrogen dioxide in the presence of ozone and oxygen have reached a steady state.

8. The instrument of claim 1, in combination with a weather balloon.

9. The instrument of claim 1, wherein said equilibrium altering means is a UV light source, wherein said UV light source is disposed within said conduit, and wherein said conduit is equipped with a UV reflective material.

10. The instrument of claim 1, wherein the first gas sensor is selected from the group consisting of(a) amperometric sensors; (b) solid state sensors whose resistance changes when exposed to ozone; (c) stain tube sensors; and (d) acoustic wave sensors.

11. The instrument of claim 1, wherein the first gas sensor is an amperometric sensor.

12. The instrument of claim 1, wherein the instrument is adapted to take the readings of the concentration of the first gas in an air sample without the addition of a second gas from a place exterior to the reaction chamber, wherein the second gas is selected from the group consisting of nitrogen dioxide, nitrogen monoxide and ozone.

13. A method for calculating the concentration of nitrogen dioxide, nitrogen monoxide and ozone in air, the method comprising:
    activating an equilibrium altering means for changing the kinetic equilibrium between nitrogen monoxide and nitrogen dioxide in the presence of ozone and oxygen in an air sample;
    taking at least three readings of the concentration of a first gas selected from the group consisting of nitrogen dioxide, nitrogen monoxide and ozone, wherein two of the at least three readings are taken at different times after the equilibrium means is altered but before the changes caused by the equilibrium altering means reach a steady state, and wherein at least one of the at least three readings is taken after the changes caused by the equilibrium altering means reach a steady state; and
    calculating, on the basis of the at least three readings, the concentration in the air sample of nitrogen dioxide, nitrogen monoxide and ozone.

14. The method of claim 13, wherein the equilibrium altering means comprises an ultraviolet light source.

15. The method of claim 14, further comprising the step of switching the ultraviolet source on and off periodically.

16. A computer program which, when loaded onto a computer is adapted to calculate the concentration of nitrogen monoxide, nitrogen dioxide and ozone in an air sample in accordance with the method of claim 15.

17. A computer program which, when loaded onto a computer is adapted to calculate the concentration of nitrogen monoxide, nitrogen dioxide and ozone in an air sample in accordance with the method of claim 15, wherein said program is disposed on a tangible medium.

18. A computer program which, when loaded onto a computer is adapted to calculate the concentration of nitrogen monoxide, nitrogen dioxide and ozone in an air sample in accordance with the method of claim 14.

19. A computer program which, when loaded onto a computer is adapted to calculate the concentration of nitrogen monoxide, nitrogen dioxide and ozone in an air sample in accordance with the method of claim 14, wherein said program is disposed on a tangible medium.

20. The method of claim 13, wherein the at least three readings are taken at distinct points in time, and wherein the concentration of the first gas at the distinct points in time is used to calculate the rate at which the balance between nitrogen dioxide and nitrogen monoxide changes in response to the effects of the equilibrium altering means.

21. A computer program which, when loaded onto a computer is adapted to calculate the concentration of nitrogen monoxide, nitrogen dioxide and ozone in an air sample in accordance with the method of claim 1.

22. A computer program which, when loaded onto a computer is adapted to calculate the concentration of nitrogen monoxide, nitrogen dioxide and ozone in an air sample in accordance with the method of claim 20, wherein said program is disposed on a tangible medium.

23. The method of claim 13, wherein the at least three readings are of ozone concentration.

24. A computer program which, when loaded onto a computer is adapted to calculate the concentration of nitrogen monoxide, nitrogen dioxide and ozone in an air sample in accordance with the method of claim 23.

25. A computer program which, when loaded onto a computer is adapted to calculate the concentration of nitrogen monoxide, nitrogen dioxide and ozone in an air sample in accordance with the method of claim 23, wherein said program is disposed on a tangible medium.

26. The method of claim 13, further comprising the steps of allowing for the effects of at least one factor, which factor is selected from the group consisting of temperature and pressure, on the equilibrium between nitrogen dioxide and nitrogen monoxide.

27. A computer program which, when loaded onto a computer is adapted to calculate the concentration of nitrogen monoxide, nitrogen dioxide and ozone in an air sample in accordance with the method of claim 26.

28. A computer program which, when loaded onto a computer is adapted to calculate the concentration of nitrogen monoxide, nitrogen dioxide and ozone in an air sample in accordance with the method of claim 26, wherein said program is disposed on a tangible medium.

29. A computer program which, when loaded onto a computer is adapted to calculate the concentration of nitrogen monoxide, nitrogen dioxide and ozone in an air sample in accordance with the method of claim 13.

30. A computer program which, when loaded onto a computer is adapted to calculate the concentration of nitrogen monoxide, nitrogen dioxide and ozone in an air sample in accordance with the method of claim 13, wherein said program is disposed on a tangible medium.

31. A method for calculating the concentration of nitrogen dioxide, nitrogen monoxide and ozone in an air sample, the method comprising:
    changing the kinetic equilibrium between nitrogen monoxide and nitrogen dioxide in the presence of ozone and oxygen in the air sample by activating a UV source;
    taking at least three readings of the concentration of a first gas selected from the group consisting of nitrogen dioxide, nitrogen monoxide and ozone, wherein at least two of the at least three readings are taken before the changes caused by the UV source reach a steady state and wherein at least one of the readings is taken after the changes caused by the UV source reach a steady state; and
    calculating, on the basis of the at least three readings, the concentration in the air sample of nitrogen dioxide, nitrogen monoxide and ozone.

32. The method of claim 31, wherein the UV source is periodically turned on and off.

33. The method of claim 32, wherein the ozone concentration in the air sample is monitored while the UV source is periodically turned on and off.

34. The method of claim 32, wherein the first gas is ozone.

* * * * *